United States Patent
Yu et al.

(10) Patent No.: US 10,842,422 B2
(45) Date of Patent: Nov. 24, 2020

(54) COMPACT LOW-COST FIBERLESS DIFFUSE SPECKLE CONTRAST FLOW-OXIMETER

(71) Applicant: University of Kentucky Research Foundation, Lexington, KY (US)

(72) Inventors: Guoqiang Yu, Lexington, KY (US); Chong Huang, Lexington, KY (US); Jeffrey Todd Hastings, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 558 days.

(21) Appl. No.: 15/655,988

(22) Filed: Jul. 21, 2017

(65) Prior Publication Data
US 2018/0020962 A1    Jan. 25, 2018

Related U.S. Application Data

(60) Provisional application No. 62/365,119, filed on Jul. 21, 2016.

(51) Int. Cl.
*A61B 5/1455* (2006.01)
*A61B 5/0205* (2006.01)
(Continued)

(52) U.S. Cl.
CPC ........ *A61B 5/14552* (2013.01); *A61B 5/0059* (2013.01); *A61B 5/0205* (2013.01);
(Continued)

(58) Field of Classification Search
CPC . A61B 5/14552; A61B 5/0059; A61B 5/6814; A61B 5/6824; A61B 5/0261; A61B 5/0205; G01N 2021/479
See application file for complete search history.

(56) References Cited

U.S. PATENT DOCUMENTS

| 6,122,042 A | 9/2000 | Wunderman et al. |
| 6,241,663 B1 | 6/2001 | Wu et al. |

(Continued)

FOREIGN PATENT DOCUMENTS

| EP | 3015848 A1 | 5/2016 |
| WO | WO200173405 A2 | 10/2001 |
| WO | WO2015127436 A2 | 8/2015 |

OTHER PUBLICATIONS

Shang, Y, Li T, Chen L, Lin Y, Toborek M and Yu G, Extraction of diffuse correlation spectroscopy flow index by integration of Nth-order linear model with Monte Carlo simulation, Applied Physics Letters. 2014, 104:193703.

(Continued)

*Primary Examiner* — Eric F Winakur
*Assistant Examiner* — Abid A Mustansir
(74) *Attorney, Agent, or Firm* — King & Schickli, PLLC

(57) ABSTRACT

A low-cost compact fiberless diffuse speckle contrast flow-meter includes a small laser diode and a 2-dimensional imaging device such as a charge coupled device (CCD) or complementary metal oxide semiconductor (CMOS) for directly contacting the tissue and measuring a parameter such as blood flow in a deep/thick volume of tissue (up to 10 mm depth). The small laser diode is fixed at a certain distance (0 to 20 mm) from the imaging device and directly contacts the tissue. Light emitted from the laser diode penetrates through the tissue and reflects back to the imaging device without passing through any lenses or fibers. One or more additional laser diodes may be added for producing light at different wavelengths, and the combination of measurements taken by the imaging device at the different wavelengths allows for measuring additional parameters, such as both blood flow and blood oxygenation.

22 Claims, 11 Drawing Sheets

(51) Int. Cl.
 A61B 5/026 (2006.01)
 A61B 5/00 (2006.01)
 G01N 21/47 (2006.01)
(52) U.S. Cl.
 CPC .......... *A61B 5/0261* (2013.01); *A61B 5/6814* (2013.01); *A61B 5/6824* (2013.01); *G01N 2021/479* (2013.01)

(56) References Cited

U.S. PATENT DOCUMENTS

| | | | |
|---|---|---|---|
| 6,643,531 B1* | 11/2003 | Katarow | A61B 5/1172 600/323 |
| 6,941,162 B2* | 9/2005 | Fudge | A61B 5/14552 221/26 |
| 7,203,345 B2 | 4/2007 | Rowe et al. | |
| 7,315,752 B2 | 1/2008 | Kraemer et al. | |
| 7,499,739 B2 | 3/2009 | Sweitzer et al. | |
| 7,604,591 B2 | 10/2009 | Uchiyama et al. | |
| 7,697,966 B2 | 4/2010 | Monfre et al. | |
| 8,082,015 B2 | 12/2011 | Yodh et al. | |
| 8,219,172 B2 | 7/2012 | Schurman et al. | |
| 8,750,954 B2 | 6/2014 | Petersen et al. | |
| 8,792,948 B2 | 7/2014 | Segman | |
| 8,831,700 B2 | 9/2014 | Schurman et al. | |
| 8,892,192 B2 | 11/2014 | Cuccia et al. | |
| 9,179,874 B2 | 11/2015 | Gonopolskiy et al. | |
| 9,282,905 B2 | 3/2016 | Wang | |
| 9,408,571 B2 | 8/2016 | Gilgunn et al. | |
| 9,487,398 B2 | 11/2016 | Rowe et al. | |
| 9,510,758 B2 | 12/2016 | Warger, II et al. | |
| 9,538,926 B2 † | 1/2017 | Durduran | |
| 10,194,808 B1* | 2/2019 | Thompson | A61B 5/02028 |
| 2005/0154294 A1 | 7/2005 | Uchiyama et al. | |
| 2006/0063995 A1* | 3/2006 | Yodh | A61B 5/14551 600/323 |
| 2013/0204112 A1* | 8/2013 | White | A61B 5/0261 600/407 |
| 2014/0206980 A1* | 7/2014 | Lee | A61B 5/0261 600/407 |
| 2014/0213891 A1 | 7/2014 | Gilgunn et al. | |
| 2014/0323879 A1 | 10/2014 | Seetamraju et al. | |
| 2015/0011852 A1 | 1/2015 | Van Kesteren et al. | |
| 2015/0073271 A1 | 3/2015 | Lee et al. | |
| 2015/0190079 A1 | 7/2015 | Yamaji et al. | |
| 2016/0073954 A1 | 3/2016 | Meitav | |
| 2016/0106325 A1 | 4/2016 | Kang et al. | |
| 2016/0113504 A1* | 4/2016 | Rege | A61B 5/489 600/479 |
| 2016/0157736 A1 | 6/2016 | Huang et al. | |
| 2016/0242683 A1 | 8/2016 | Ishiguro et al. | |
| 2016/0278715 A1 | 9/2016 | Yu et al. | |
| 2016/0338623 A1 | 11/2016 | Tholl et al. | |
| 2016/0353997 A1 | 12/2016 | Yodh et al. | |
| 2016/0361017 A1 | 12/2016 | Busch, Jr. et al. | |

OTHER PUBLICATIONS

Shang, Y and Yu G, A Nth-order linear algorithm for extracting diffuse correlation spectroscopy blood flow indices in heterogeneous tissues, Applied Physics Letters, 2014, 105:133702.

Shang, Y, Cheng R, Dong L, Ryan SJ, Saha SP and Yu G, Cerebral monitoring during carotid endarterectomy using near-infrared diffuse optical spectroscopies and electroencephalogram, Phys Med Biol., 2011; 56:3015-3032.

Cheng, R, Shang Y, Hayes D, Saha SP and Yu G, Noninvasive optical evaluation of spontaneous low frequency oscillations in cerebral hemodynamics, Neuroimage, 2012; 62:1445-1454.

Cheng, R, Shang Y, Wang SQ, Evans JM, Rayapati A, Randall DC and Yu G, Near-infrared diffuse optical monitoring of cerebral blood flow and oxygenation for the prediction of vasovagal syncope, J Biomed Opt., 2014; 19.

Shang, Y, Zhao, Y. Cheng, Y Dong L, Irwin D, Yu G, Portable optical tissue flow oximeter based on diffuse correlation spectroscopy, Optics Letters, 34(22), 3556-3558 (2009).

Liu, H, Boas DA, Zhang Y, Yodh AG and Chance B, Determination of optical properties and blood oxygenation in tissue using continuous NIR light, Phys Med Biol., 1995; 40:1983-93.

Gurley, K, Shang Y and Yu G. Noninvasive optical quantification of absolute blood flow, blood oxygenation, and oxygen consumption rate in exercising skeletal muscle, J Biomed Opt., 2012;17:075010.

Shang, Y, Chen L, Toborek M and Yu G. Diffuse optical monitoring of repeated cerebral ischemia in mice. Opt Express. 2011;19:20301-20315.

Chen, L, Shang Y, Sipos KE, Saatman KE, Yu G and Toborek M. Novel experimental model for repeated forebrain ischemia-reperfusion, Journal of experimental stroke and translational medicine, 2012;5:1-10.

Cheung et al. (Jul. 6, 2001) In vivo cerebrovascular measurement combining diffuse near-infrared absorption and correlation spectroscopies. Physics in Medicine and Biology, vol. 46, pp. 2063-2065. stacks.iop.org/PMB/46/2053.†

Atchia et al. (Feb. 11, 2013) Rapid multiexposure in vivo brain imaging system using vertical cavity surface emitting lasers as a light source. Applied Optics, vol. 52, No. 7, pp. C64-C71. DOI:10.1364/AO.52.000C64.†

Sigal et al. (Aug. 22, 2106) Imaging brain activity during seizures in freely behaving rats using a miniature multi-modal imaging system. Biomedical Optics Express, vol. 7, No. 9, pp. 3596-3609. DOI:10.0164/BOE.7.003596.†

Dragojevic et al. (Oct. 15, 2016) Speckle contrast optical spectroscopy of the adult brain with a novel, compact system. Abstract Book, fNIRS 2016, Oct. 13-16, 2016, Universite Paris Descartes, 12 rue de l'Ecole de Medecine, Paris. p. 66.†

Hollman et al. (Apr. 1, 2017) A diffuse optical method and a compact device for measuring cerebral blood flow in adult human brain. Journal of Cerebral Blood Flow & Metabolism, vol. 37 (1_suppl), p. 293, Poster No. PS03-007. DOI:10.1177/0271678X17695987.†

Bi et al. (Apr. 23, 2013) Deep tissue flowmetry based on diffuse speckle contrast analysis. Optics Letters, vol. 38, No. 9, pp. 1401-1403. DOI:10.0364/OL.38.001401.†

Bi et al. (Sep. 20,2013) Multi-channel deep tissue flowmetry based on temporal diffuse speckle contrast analysis. Optics Express, vol. 21, No. 19, pp. 22854-22861. DOI:10.1364/OE.21.022854.†

Valdes et al. (Jul. 23, 2014) Speckle contrast optical spectroscopy, a non-invasive, diffuse optical method for measuring microvascular blood flow in tissue. Biomedical Optics Express, vol. 5, No. 8, pp. 2769-2784. DOI:10.1364/BOE.5.002769.†

\* cited by examiner
† cited by third party

COMPACT LOW-COST FIBERLESS DIFFUSE SPECKLE CONTRAST FLOW-OXIMETER

This application claims priority to U.S. PROVISIONAL Application Ser. No. 62/365,119, filed Jul. 21, 2016, the disclosure of which is hereby incorporated by reference.

TECHNICAL FIELD

This invention generally relates to a device for noninvasively measuring tissue blood flow and oxygenation, and more particularly, to a compact fiberless diffuse speckle contrast flow-oximeter for measuring blood flow and oxygenation at relatively deep tissues below skin level.

BACKGROUND OF THE INVENTION

The measurements of blood flow (BF) and oxygenation alterations in the tissue helps characterize many diseases representing with tissue ischemia and hypoxia such as cerebral vascular disease, peripheral artery disease, and cancer. For example, more than 4 million babies are born annually in the United States and ~11% of those (440,000) are born premature and admitted to neonatal intensive care units (NICUs). The total societal economic cost of preterm birth is estimated at 26 billion dollars including medical costs, early intervention, special education services, and lost household and labor market productivity. Although significant progress has been made in the care of preterm infants, they continue to suffer from significant morbidities and comorbidities. Approximately 65% of infants born between 25 and 28 weeks of gestational age (GA), and 85% of those born at GA of <24 weeks have patent ductus arteriosus (PDA) at first week of life. PDA leads to shunting of blood between the systemic and the pulmonary circulations, which is associated with adverse outcomes including prolonged assisted ventilation and higher rates of death, bronchopulmonary dysplasia, pulmonary hemorrhage, necrotizing enterocolitis, impaired renal function, intraventricular hemorrhage, periventricular leukomalacia, and cerebral palsy. Because of these associated complications, the majority of infants at GA of ≤28 weeks receive medical or surgical therapy in an attempt to close the PDA. Currently, the gold standard for PDA diagnosis is echocardiography, but often clinical symptoms are not associated with echocardiography findings.

Compared to large imaging modalities such as computed tomography (CT), magnetic resonance imaging (MRI), and positron emission tomography (PET) for BF measurements, optical instruments are relatively portable, fast, continuous, and inexpensive. Optical techniques based on dynamic light scattering are the most common methods for BF measurements including laser speckle contrast imaging (LSCI) and diffuse correlation spectroscopy/tomography (DCS/DCT). Each technique, however, has key issues that limit its application. LSCI uses wide-field illumination and charge-coupled-device (CCD) detection of spatial laser speckle contrasts to achieve rapid high-resolution 2-D mapping of blood flow in superficial tissues (depth <1 mm). By contrast, DCS/DCT uses coherent near-infrared (NIR) point-source illumination and single-photon-counting avalanche photodiodes (APDs) to accommodate spectroscopic or tomographic measurements of BF variations in deep tissues (up to ~15 mm). However, the use of expensive long-coherence length lasers (e.g. DL785-120, Crystalaser) and APDs (e.g. SPCM-NIR, Pacer) limits its spatial-temporal resolution and increases instrumentation cost.

There have been a few recent technical advancements towards BF measurements in deep tissues with coherent NIR point-source illumination and high sensitive CCD detection (e.g., electron multiplication CCD (EMCCD)), where the diffuse speckle contrast spectroscopy/tomography extracts deep tissue BF information using the relationship between diffuse speckle contrast parameters and DCS/DCT theory. Hundreds of detectors provided by the CCD significantly improve the spatial and temporal resolution and reduce the instrumentation cost and dimension. In these measurement setups, a CCD sensor is generally connected with optical lenses or optical fibers to detect diffuse speckle contrast variations induced by the motion of red blood cells in the tissue (i.e., blood flow). A long-coherence length laser or a small laser diode are usually coupled to a lens system or an optical fiber to deliver NIR light to the target tissue. However, these noncontact (through optical lenses) or semi-noncontact measurements (through optical lenses and optical fibers) with lasers and CCD cameras make the measurements very sensitive to motion artifacts and ambient light. In addition, EMCCDs and long-coherence length lasers used are still quite expensive and large.

There are very few tools available for continual bedside assessment of neonatal brain health, which can be impacted by the PDA and associated treatment procedures. Transcranial Doppler (TCD) probe is the commonly used bedside method to evaluate cerebral blood flow velocity (CBFV) in large arteries, but this method is difficult to perform continuously on neonatal heads and may not agree with CBF in local cerebral microvasculature. Near-infrared spectroscopy (NIRS) provides a continuous measurement of tissue oxygenation saturation ($StO_2$) in local cerebral microvasculature. However, there is a critical need for more evidence concerning sensitivities and accuracies before applying these measurements to clinical practice. A more recently developed method of near-infrared DCS provides a direct cerebral blood flow (CBF) measurement in local cerebral microvasculature. DCS monitors temporal speckle fluctuations resulting from moving red blood cells (RBCs) and has proven to be a valid assessment of CBF variations in the brains of adults and children. DCS has been combined with NIRS into hybrid instruments for simultaneous measurements of $StO_2$ and CBF, which allows for the derivation of cerebral metabolic rate of oxygen ($CMRO_2$). For example, a hybrid NIRS/DCS instrument was used to longitudinally obtain data from premature neonates' brains and results showed a steady decrease in $StO_2$ and steady increases in CBF and $CMRO_2$ during the first six weeks of life, which are in qualitative agreement with physiological expectations. Also, in an animal model of neonatal brain injury, it has been shown that $CMRO_2$, and not $StO_2$, correlated with the duration of cerebral ischemia. These results suggest that multiple hemodynamic/metabolic variables provide more comprehensive assessment of neonatal brain health than a single parameter alone. However, as with blood flow measurements, the use of DCS in measuring other parameters retains the shortcomings noted above.

Accordingly, a need has been identified for a system for measuring multiple hemodynamic/metabolic variables, such as blood flow and blood oxygenation measurements in deep tissues, including through the skull, which addresses these and other shortcomings of current technologies.

SUMMARY OF THE INVENTION

An object of the disclosure is to provide a probe for use in measuring a hemodynamic parameter within a tissue of a subject. For example, the hemodynamic parameter may be blood flow and/or blood oxygenation through the tissue. The probe may include a laser diode for emitting light into the tissue of the subject, and a bare imaging device adapted to contact the tissue of the subject and receive light reflected from the tissue to detect diffuse speckle contrast variations in the tissue for measurement of the hemodynamic parameter. The bare imaging device may be a 2-dimensional array imaging device.

In one aspect, the probe may include no optical fiber. This may include no optical fiber associated with the laser diode or the bare imaging device.

The laser diode may emit near-infrared light at a fixed wavelength. This fixed wavelength may range from 700-900 nm for the measurement of blood flow. For example, the wavelength may be 785 nm. The laser diode may produce a short coherence length through human tissue. For example, the coherence length of the laser diode may be 10 cm-100 cm. The laser diode may be adapted to contact the tissue of the subject.

In a further aspect, the probe may include a retainer for retaining the laser diode and the bare imaging device at fixed positions relative to each other. For example, the laser diode and the bare imaging device may be fixed relative to one another at a distance of between 0 and 20 mm. In one embodiment, this distance may be between 13 mm and 18 mm. The retainer may comprise a pad, such as a foam pad, or a plate. The retainer may include one or more receivers, such as holes, apertures, or recesses, for retaining the laser diode and the bare imaging device.

The bare imaging device may be adapted to receive the light diffused and reflected from the tissue without passing through any lenses prior to receiving the light. Accordingly, the imaging device may be considered "bare," as it may contact the tissue of the subject.

The probe may further include or be adapted to connect with a controller for controlling the function of the bare imaging device. The controller may be remote from the bare imaging device. For example, in the case of the use of a retainer, the controller may not be in contact with the retainer. In one aspect, the controller may be connected to the bare imaging device via electrical wires. In another aspect, the controller may be wirelessly connected to the bare imaging. The controller may comprise a computer, a laptop, or other mobile device.

The bare imaging device may comprise a charge coupled device. In another aspect, the bare imaging device may comprise a complementary metal oxide semiconductor. In one aspect, one or more heat sinks and/or a fan may be connected to the bare imaging device for dissipation of heat.

In another embodiment, a probe is disclosed for use in measuring at least one hemodynamic parameter within a tissue of a subject. The probe may comprise a first laser diode adapted for emitting light into the tissue of the subject at a first wavelength, and a second laser diode adapted for emitting light into the tissue of the subject at a second wavelength different from the first wavelength. The probe may further include a bare imaging device adapted to contact the tissue of the subject and receive light diffused and reflected from the tissue to detect diffuse speckle contrast variations in the tissue for measurement of the at least one hemodynamic parameter. The probe may additionally include a retainer adapted to receive and maintain a constant distance from each of the first laser diode and the second laser diode to the bare imaging device, said retainer including a contact surface adapted to contact the tissue of the subject, and may be further adapted to maintain the bare imaging device in contact with the tissue with no lens therebetween.

In one aspect, the probe includes no optical fiber.

The bare imaging device may comprise a charge coupled device. In another aspect, the bare imaging device may comprise a complementary metal oxide semiconductor.

One or more heat sinks may be provided to assist in dissipating heat produced by the bare imaging device. For instance, one or more heat sinks may be in contact with the bare imaging device. In another aspect, a fan may be included for heat dissipation with respect to the bare imaging device. In another aspect, a low-power imaging device may be included without the need of heat dissipation.

In a further embodiment, a method is disclosed for measuring at least one hemodynamic parameter within a tissue of a subject. The method may include emitting light at a first wavelength from a first laser diode into the tissue without fiber coupling, said light not received through an optical cable, placing a bare imaging device in contact with the tissue with no lens therebetween, and measuring reflected light from the tissue to detect diffuse speckle contrast variations in the tissue in order to measure the at least one hemodynamic parameter. The first laser diode may produce a short coherence length (e.g. 10 cm-100 cm) when said light is emitted directly without fiber coupling through the tissue.

In one aspect, the method may further include the step of emitting light at a second wavelength from a second laser diode into the tissue. In this aspect, the measuring step may comprise measuring reflected lights from the tissue from the first laser diode and the second laser diode.

In a further aspect, the method may include the step of attaching each of the first laser diode and the bare imaging device to a retainer in order to maintain a fixed distance therebetween. In the instance of the inclusion of the second laser diode, the method may include attaching the second laser diode to the retainer in order to maintain a fixed distance between the second laser diode and the bare imaging device. The fixed distance from the first laser diode (and/or from the second laser diode) to the bare imaging device may be between 0 and 20 mm, or more narrowly, between 13 mm and 18 mm.

DETAILED DESCRIPTION OF THE INVENTION

Figure 1:
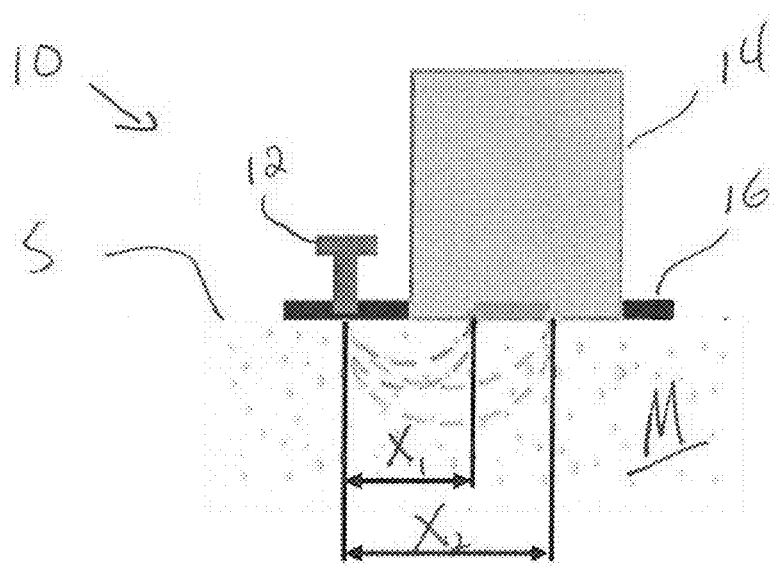
FIG. 1 is a schematic of a contact diffuse speckle contrast flowmeter (DSCF) probe.

The description provided below and in regard to the figures applies to all embodiments unless noted otherwise, and features common to each embodiment are similarly shown and numbered.

In one aspect, the current disclosure identifies a low-cost compact fiberless diffuse speckle contrast flowmeter (DSCF) in order to measure blood flow. The DSCF may comprise a probe 10 including a laser diode 12 and a bare imaging device 14. This bare imaging device 14 may comprise a 2-dimensional array imaging device. For example, the bare imaging device 14 may comprise a charge-coupled device (CCD) or a complementary metal oxide semiconductor (CMOS) imaging device.

The use of a small laser diode 12, especially one with a short coherence length, allows for use of the probe without a fiber optic cable. For purposes of this disclosure, the term "short coherence length" is anything with a coherence length between 10 cm-100 cm. In one aspect, the laser diode may output a wavelength of between 700 and 900 nm (e.g. 785 nm), at a power of below 25 mW, and may have a diameter of 5.6 mm (e.g. L785P25, Thorlabs, NJ). A wavelength of 700-900 nm (e.g. 785 nm) may be used for measuring blood flow, and two laser diodes with different wavelengths may be used for measuring a different tissue parameter (e.g. wavelengths of 785 nm and 854 nm for measuring oxygenation). More laser diodes (>2) can be used to improve measurement accuracy. The laser diode 12 may have a short coherence length.

In one aspect, the bare imaging device 14 may comprise a sensor, a chip, or a combination of the two. For instance, the bare imaging device 14 may comprise a bare imaging chip 20 (which may be a CCD chip or a CMOS chip), including a bare imaging sensor 22 (which may be a CCD sensor or a CMOS sensor), approximately 40×32 mm$^2$, with a resolution of 1296×964 pixels. In a further aspect, the imaging device 14 may include no lenses. The lack of lenses indicates that the bare imaging device 14, including the bare imaging sensor chip 20, may be directly placed on the tissue surface S for contact measurements of BF variations in deep tissues (e.g. approximately up to 10 mm below tissue surface, such as for example, 8 mm below tissue surface). In other words, the bare imaging device may be described as a contact sensor because it may contact the tissue through which BF is measured.

One embodiment of the DSCF probe 10 is illustrated in FIG. 1. As illustrated, the DSCF probe 10 may be placed on the surface S of turbid media M (e.g., tissue phantoms or human tissues) for flow measurements. The laser diode 12 may act as a light source, and may be placed a known distance away from the bare imaging device 14. For example, the laser diode 12 may be placed at a known distance away from an imaging sensor 22 (e.g. a CCD sensor or CMOS sensor) of the bare imaging device 14. As illustrated, this distance may be between $X_1$ and $X_2$. This distance may be referred to as the source-detector (S-D) distance. In one aspect of the invention, the S-D distance may vary from 0 to 20 mm, or more narrowly from 13 mm to 18 mm. Based on photon diffusion theory, NIR light penetration depth in tissues is approximately one half of the S-D distance. This is because light transport through tissue is diffuse rather than straightforward. Therefore, penetration depth of light and the ability to take measurements based thereon depend on the S-D separation distance (i.e. about half of the S-D separation). The range of S-D separation that may be used depends on the arrangement of the laser diode 12 and the imaging device 14, as well as the light intensity and imaging device sensitivity. In the present invention, typical S-D distances may be from 0 mm-20 mm. Therefore, the penetration depth may be from 0 mm-10 mm.

A retainer 16 may be provided for maintaining relative position between the laser diode 12 and the bare imaging device 14. The retainer 16 may be in the form of a pad, a plate, a block, or a film, which may include one or more receivers for receiving the laser diode 12 and the bare imaging device 14. For example, the retainer 16 may comprise a foam pad with an aperture or retaining space for each of the laser diode 12 and the bare imaging device 14. In one aspect, a thin film may be provided (not pictured) to prevent the bare imaging sensor 22 and/or the bare imaging chip 20 from being shorted by the turbid media M.

Figure 2:
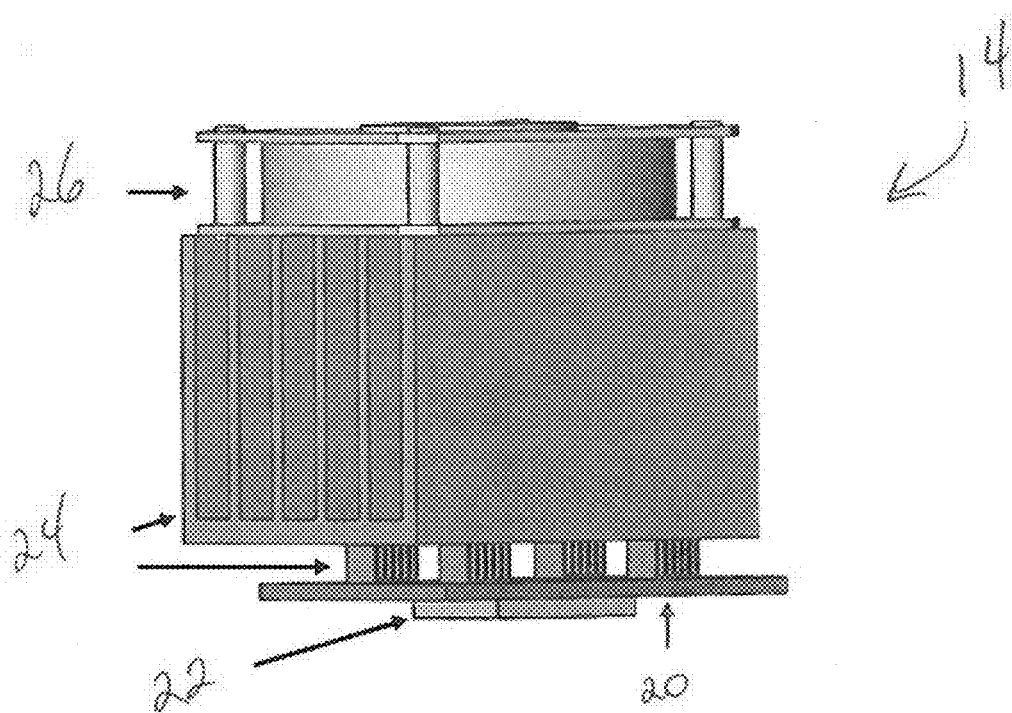
FIG. 2 illustrates an imaging device of the DSCF of FIG. 1.

With further reference to FIG. 2, one embodiment of the bare imaging device 14 is illustrated. The imaging device 14 may include the bare imaging sensor 22 and the bare imaging chip 20, which may be located at the bottom of the bare imaging device 14, such as for being placed in contact with the surface of the tissue to be measured. The bare imaging chip 20 may operate as a plurality of flow detectors. For example, each window of 7×7 pixels may act as a single detector. This may allow a single bare imaging chip 20 to include hundreds of detectors. The bare imaging chip 20 may be connected and controlled by an external controller, such as a computer, a laptop, or other mobile device. In one aspect, the connection may be through a Universal Serial Bus cable (not shown).

One issue with a CCD or CMOS based contact measurement is that some CCD or CMOS chips may accumulate heat. This accumulation of heat from a bare imaging sensor/chip, which is directly contacted to the surface of target media, could cause discomfort to a subject or may interfere with probe efficacy. In order to spread the heat that may be generated by a CCD or CMOS chip, multiple small heat sinks 24 may be included. The heat sinks may be in the form of a plate or fin. The heat sinks 24 may be attached, such as by a thermal compound, to the integrated circuits of the imaging chip. For example, the heat sinks may be approximately 6×6 mm². A fan 26 may also be included for further enhancing heat dissipation. One or more additional heat sinks, such as a 40×40 mm heat sink, may be connected to the fan 26 to further assist in heat dissipation.

In another aspect, the potential accumulation of heat may be addressed by the use of an imaging device 14 with a low power consumption. For example, a small CMOS sensor may be used, such as the MU9PM-MBRD, by Ximea, which has a typical power consumption of 0.6 W. Another example of a CMOS chip is the NanEye by Awaiba, with a power consumption as low as 4.2 mW. With a small, low-power CMOS sensor, the size of the DSCF probe may be minimized to 6×8 mm² (e.g. using "L785P25" as a laser diode and "NanEye" as imaging device; S-D distance is set as minimal) and the generated heat may be significantly reduced. As a result, the new DSCF probe can work properly without using sinks/fans for heat dissipation.

The laser diode 12 may be inserted into a socket (e.g. S7060R, Thorlabs, NJ) and may be powered by a constant-current driver (e.g. LDC 205C, Thorlabs, NJ). The laser diode 12 may oscillate in a single transverse mode, and may support multiple longitudinal modes. In one aspect, the laser diode 12 would not be expected to exhibit a long coherence length. However, few mode lasers have complex correlation functions that are not well described by a single coherence length. To assess this, the laser diode 12 may be placed in a Michelson interferometer and operated under the same conditions as in the DSCF probe 10 (constant 50 mA drive current with no active temperature stabilization). When this was done with the laser diode identified herein, high-visibility (>0.8) fringes were observed at many path-length differences between 0 and 400 mm (limit of test). Thus, the laser's coherence is entirely sufficient for the S-D separations described herein.

One distinction between a CCD or CMOS based imaging device of the DSCF and the APD detection in DCS is the transition from measurements of slower temporal speckle fluctuations with sufficient signal-to-noise ratio (i.e. hundreds of milliseconds for DCS probes) to faster spatial speckle fluctuations (i.e. a few milliseconds for the DSCF probe). To measure speckle fluctuations, lasers with certain coherence length are needed. In general, the coherence length of a laser must be longer than the photon path length throughout the tissue, which is generally several time (e.g. five times for muscles) longer than the distance between the source and the detector. For example, the maximal S-D distance for the DSCF may be approximately 20 mm, so a laser diode for a DSCF probe should have a coherence length of approximately 10 cm at least.

In order to catch up with the slower temporal fluctuations (i.e. mathematically calculating the temporal autocorrelation function), DCS uses a laser with a coherence length longer than several meters (which has been experimentally determined). The long coherence length requirement makes the laser required for DCS larger in dimension (so that it cannot be placed on the tissue directly) as well as expensive. The light from such long coherence length lasers must also be passed through an optical fiber. However, an optical fiber is rigid and lacks flexibility desired for a probe that may positionally manipulated easily.

By contrast, DSCF measures fast spatial speckle fluctuations within only about 5 ms, mathematically calculating $$K_s(r) = \frac{\sigma_s}{\langle I \rangle}$$

where $\sigma_s$ is the spatial standard deviation and $\langle I \rangle$ is the mean intensity in a 7×7 pixel window). Therefore, a laser diodes with a coherence length longer than tens of centimeters can be used for DSCF. Most laser diodes meet this specification. For purposes of this disclosure, a laser diode for use with a DSCF probe need only have a low coherence length (i.e. greater than 10 cm, but less than 100 cm). And laser diodes are significantly smaller in size than a laser with long coherence length required for a DCS probe. Therefore, the laser diode can be placed directly on the tissue of a subject without the use of any optical fibers. Another advantage to the use of a bare CCD or CMOS as compared to a larger APD is the elimination of fiber coupling. The size of an APD is large and cannot be placed directly on the tissue. So the APD has to be connected to an optical fiber as well. The bare CCD or CMOS does not require any such optical fiber. This provides flexibility in the DSCF probe that is not available in a DCS probe, while still allowing for accuracy of measurements.

In order to calibrate/validate the DSCF probe 10, concurrent flow measurements on liquid tissue phantoms against a noncontact CCD-based diffuse speckle contrast probe and a standard contact DCS probe were conducted. The liquid tissue phantom comprised distilled water, India ink, and Intralipid, which has been commonly used for the calibration of flow measurement techniques. India ink is used to manipulate the absorption coefficient $\mu_a$ while Intralipid provides particle Brownian motion (flow) and control of the reduced scattering coefficient $\mu_s'$. The absorption coefficient was set to $\mu_a$=0.03 cm$^{-1}$ and $\mu_s'$=8 cm$^{-1}$ at 785 nm to mimic the property of biological tissues. Flow variations of Intralipid particles were created by changing the phantom temperature. The temperature of the phantom was initially set up to 70° C. by an immersed heater (CH103, Ovente, Calif.), and then decreased naturally until reaching the room temperature of ~22° C. A thermometer sensor (Physitemp, NJ) was placed inside the liquid tissue phantom for temperature measurements.

Figure 3:
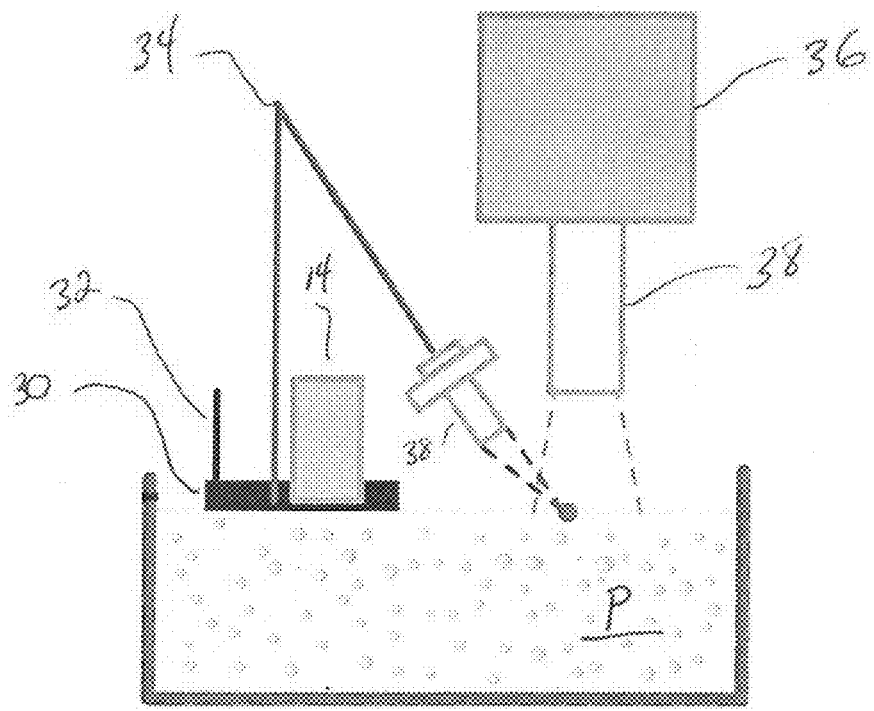
FIG. 3 is a schematic of a validity test of the imaging device of the DSCF probe of FIG. 1 in a tissue-simulating phantom, as compared to a contact diffuse correlation spectroscopy (DCS) probe and a non-contact imaging device probe.

An example of a representative schematic for a phantom experiment for testing the validity and accuracy of the DSCF is shown in FIG. 3. This phantom experiment was designed to compare the results obtained concurrently from the contact measurements using two different contact probes (i.e., DSCF and DCS) and a noncontact measurement using another CCD camera with optical lenses (e.g., FL3-FW-20S4M-C, Point Grey, BC, Canada). As shown in FIG. 3, a dual contact probe element 30 includes both the bare imaging device 14 of the DSCF (in this instance a CCD), as well as a detector fiber 32 to an APD (not illustrated) to utilize DCS. In addition, a noncontact CCD camera 36 was utilized, which included multiple lenses 38 for focusing and manipulating light source.

Figure 4:
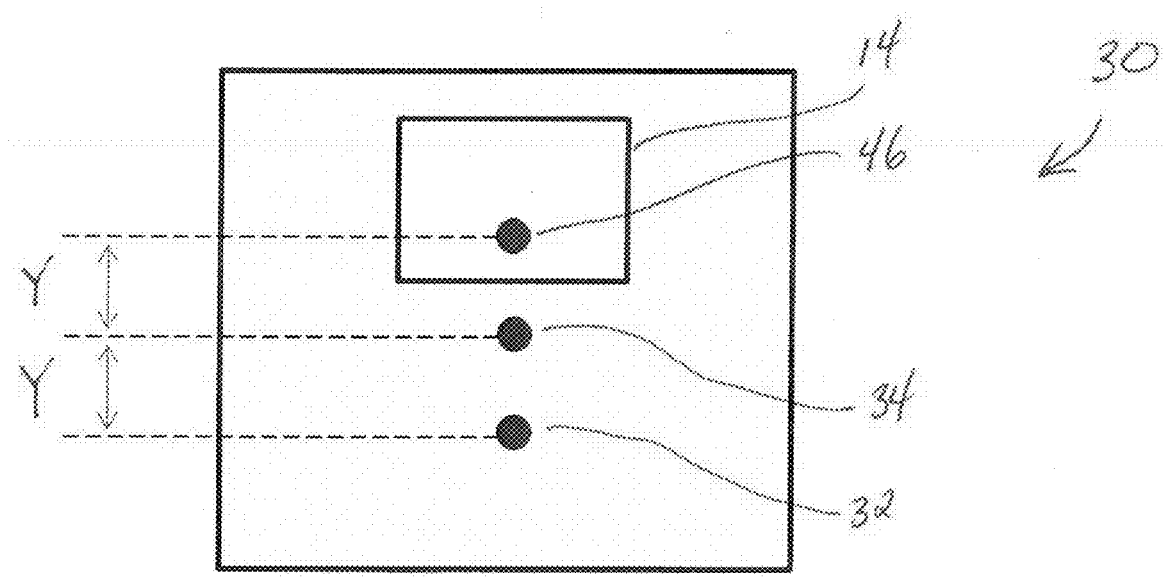
FIG. 4 is a schematic of a first dual contact probe used in the validity test of FIG. 3.

Due to the use of DCS for validation, a long-coherence length DCS laser 34 (e.g. DL785-100, CrystaLaser, NV; wavelength: 785 nm, coherence length: >5 m, power: 100 mW, dimensions: 135×36×30 mm$^3$, price: >$7K) was utilized. The DCS laser 34 delivered NIR light to the liquid tissue phantom P via a customized 1×2 fiber-based beam splitter (e.g. Fiberoptic Systems, CA). A single-mode detector fiber (e.g. SM800-5.6-125, Fibercore, CA) connected to a 4-channel APD module (e.g. SPCM-AQ4C, PerkinElmer, CA; dimensions: 150×130×34 mm$^3$, price: >$11K) and a 4-channel autocorrelation board (e.g., Flex01LQ-05, Zhu, Jixiang, NJ; price: ~$13K) was used to collect the diffused light for the contact DCS measurement as a gold standard for comparisons. An identical S-D distance Y was used for all three probes for consistency, and in this instance, an S-D distance of 15 mm was used in all three probes. The placement of the bare imaging device 14 (with its CCD detector 46, comprising a set of 7×7 pixels of the CCD) and the DCS detector fiber 32, each with respect to the long coherence length DCS laser 34 for the contact probes, can be seen in FIG. 4. During the calibration/validation procedure, thirty data points (DCS) or frames (CCDs) were concurrently collected within 15 seconds (i.e., 2 Hz sampling rate) by the three probes at each of three different temperatures (65° C., 45° C., and 25° C.). The two CCDs worked in parallel with the same exposure time of 5 ms. Room light was turned off during these measurements.

For standard DCS data analysis, flow index was extracted by fitting the autocorrelation curve whose decay rate depended on the motion of moving Intralipid particles. For DSCF data analysis, as described above, the spatial speckle contrast (K) over a selected window of 7×7 pixels was determined by calculating the ratio of standard deviation ($\sigma$) and mean ($\mu$) over these 49 pixels; i.e., K=$\sigma/\mu$. Flow-induced speckle fluctuation resulted in the reduction of laser speckle contrast in space for a given exposure time. Flow index was extracted via a nonlinear relationship between the K and flow index under semi-infinite geometry. To increase the signal-to-noise ratio (SNR) of flow detection, a 3×3 adjacent pixel window array (covering an area of ~78 µm×78 µm) with nine values of K were averaged representing one DSCF detector. The detector center was chosen at 15 mm away from the laser source, allowing a penetration depth of ~8 mm. Relative flow changes were calculated by normalizing flow data at all measurement steps (i.e., 65° C., 45° C., and 25° C.) to the averaged flow index (assigning 100%) at the last step (25° C.).

Figures 5A, 5B, 5C:
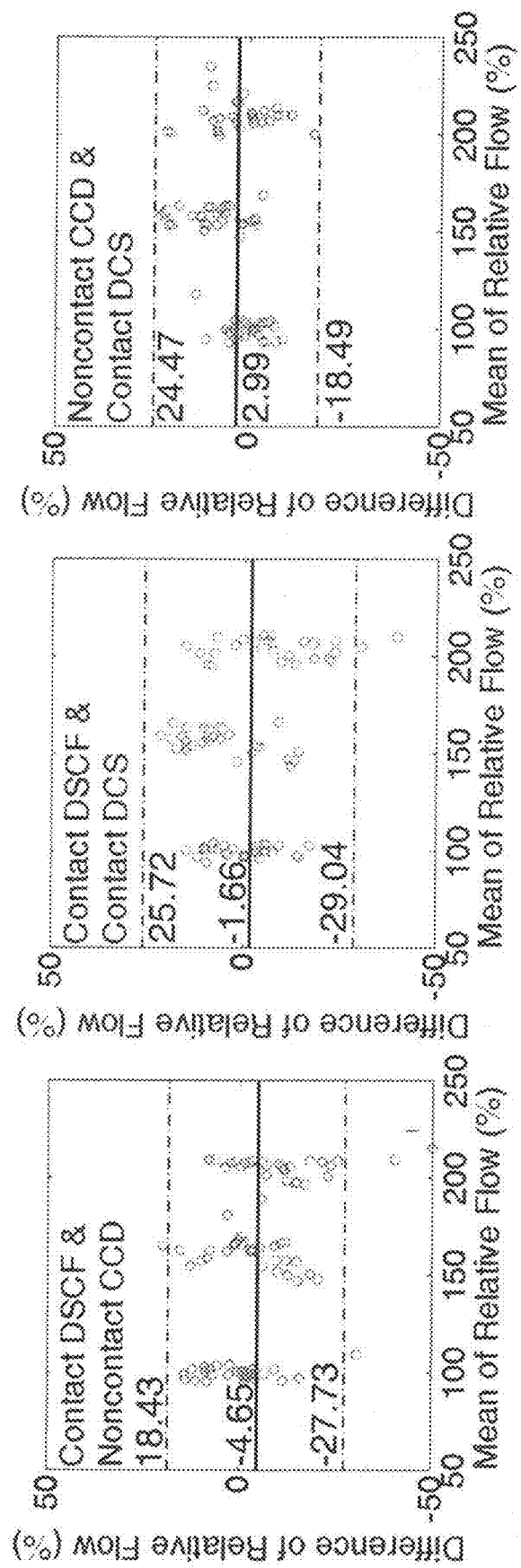
FIGS. 5*a*-5*c* are Bland-Altman plots illustrating the results of the validity test in a tissue-simulating phantom of FIG. 3.

Bland-Altman plot analysis was used to determine the agreement between different measurements and Mann-Whitney u-test was used to test the systematic difference in mean values between the measurements (i.e., the fixed bias). FIGS. 5a-5c show Bland-Altman plots for the comparisons between the two of three flow measurements by the three optical probes. Specifically, FIG. 5a illustrates a comparison of the contact DSCF probe and the non-contact CCD probe. FIG. 5b illustrates a comparison of the contact DSCF probe and the contact DCS probe. FIG. 5c illustrates a comparison of the non-contact CCD probe and the contact DCS probe. The y-axis shows the difference between the two paired measurements (A-B) and the x-axis shows the mean value of these measurements (A+B)/2. The horizontal solid line represents the mean value of (A-B) and horizontal dashed lines represent the mean values of (A-B)±1.96×standard deviation of (A-B). For a good agreement between two measurements, approximately 95% of the differences are expected to be less than 1.96 standard deviation. Good limits of agreement among these measurements (95.6% in FIG. 5a, 97.8% in FIG. 5b, and 100.0% in FIG. 5c) were observed. This experiment demonstrated that the contact and noncontact CCD-based diffuse speckle contrast measurements of flow changes generated highly consistent results (FIG. 5a), each of which also significantly agreed with the standard contact DCS measurement results (FIG. 5b and FIG. 5c).

Figure 6:
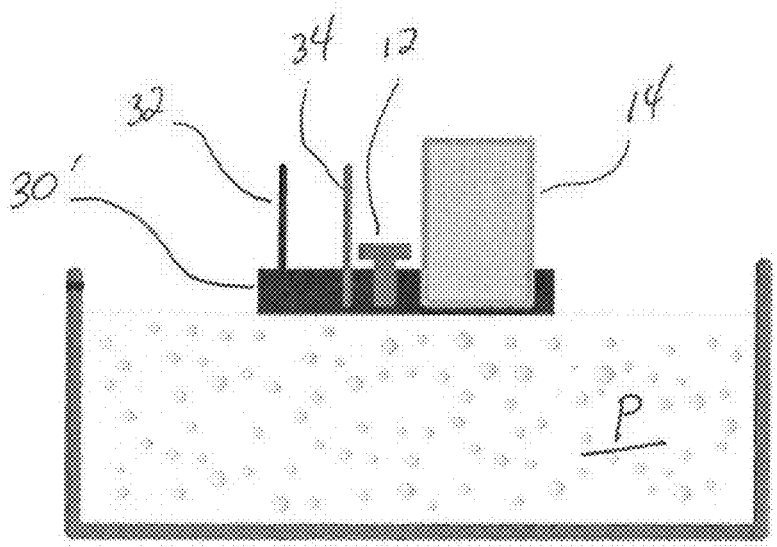
FIG. 6 is a schematic of a validity test of a laser diode of the DSCF of FIG. 1 in a tissue-simulating phantom.

A second phantom experiment, a representative schematic for which is shown in FIG. 6, was designed to compare the results obtained by the short coherence length laser diode 12 for DSCF and the long-coherence laser 34 for standard DCS. Therein, a dual contact probe 30' includes the bare imaging device 14 (again, in this case a CCD) of the DSCF probe 10 and the corresponding short coherence length laser diode 12. In addition, the dual contact probe 30' includes the long coherence length DCS laser 34 for use with the DCS detector fiber 32, which is connected to an APD (not illustrated) to utilize DCS. The dual contact probe 30' was placed in contact with a surface of the liquid tissue phantom P.

Figure 7:
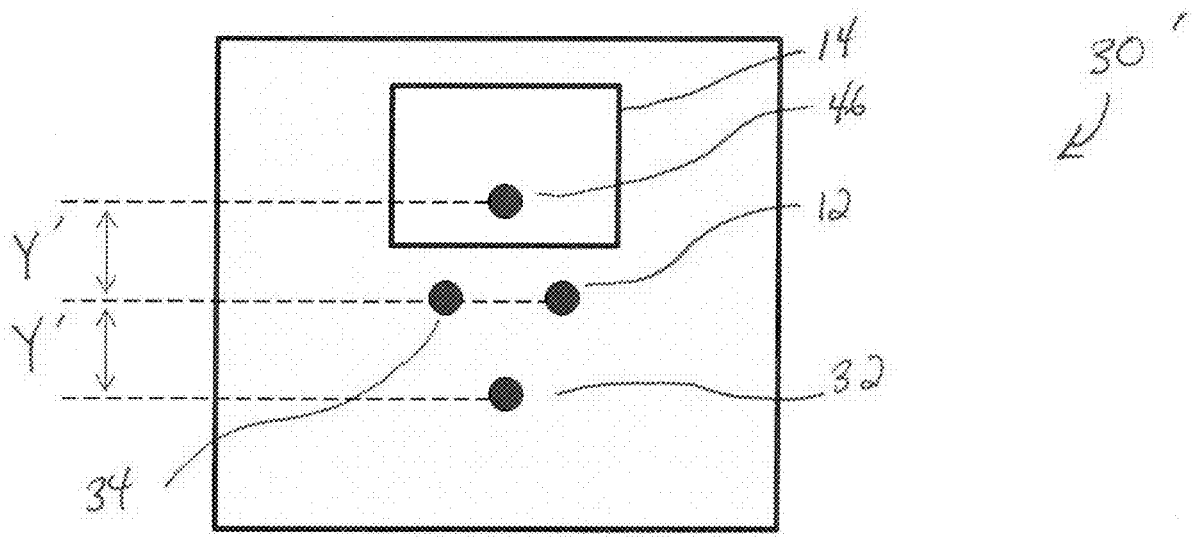
FIG. 7 is a schematic of a second dual contact probe used in the validity test of FIG. 6.

As illustrated in FIG. 7, the short coherence length laser diode 12 was placed at an identical S-D distance from the CCD detector 46 of the bare imaging device 14 as the long coherence length DCS laser was placed from the DCS detector fiber 32. This identical S-D distance is shown as Y' in FIG. 7. For the purposes of this second phantom experiment, Y' was set to 15 mm.

Experimental protocols, data collection, and data analyses were similar to those described above. For each measurement at certain temperature (i.e. 65° C., 45° C., and 25° C.), two lasers were turned on alternatively and thirty data points were collected in parallel by the DSCF and DCS detectors at the sampling rate of 2 Hz.

Figures 8A, 8B, 8C:
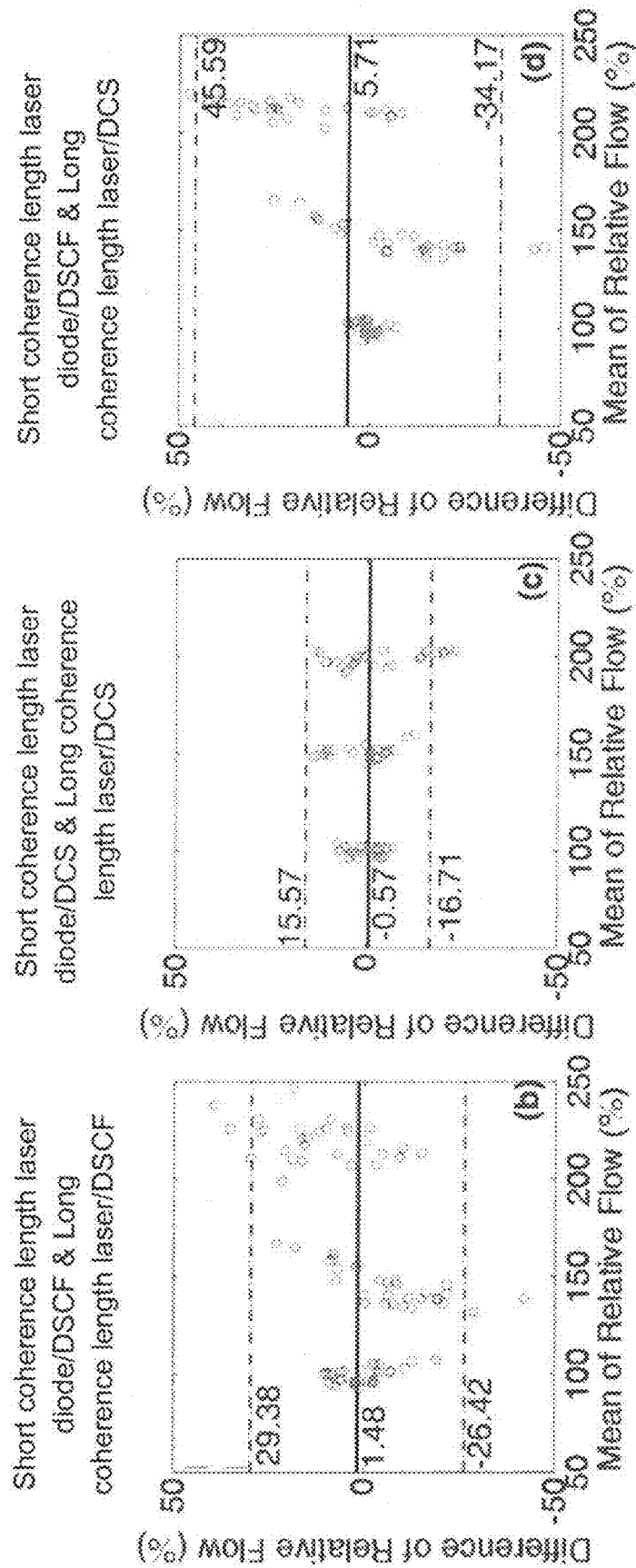
FIGS. 8*a*-8*c* are Bland-Altman plots illustrating the results of the validity test of FIG. 6.

FIGS. 8a-8c show the Bland-Altman analysis between the two of three flow measurements by different compositions of sources and detectors. Specifically, FIG. 8a illustrates a comparison of the short coherence length laser diode 12 used with the DSCF probe and the long coherence length laser 34 used with the DSCF probe (i.e. the bare CCD 14). FIG. 8b illustrates a comparison of the short coherence length laser diode 12 used with the DCS detector fiber 32 and the long coherence length laser 34 used with the DCS detector fiber 32. FIG. 8c illustrates a comparison of the short coherence length laser diode 12 used with the DSCF probe (i.e. the bare imaging device 14 using a CCD) and the long coherence length laser 34 used with the DCS detector fiber 32. Good limits of agreement among these measurements (94.4% in FIG. 8a, 94.4% in FIG. 8b and 96.7% in FIG. 8c) were observed with no significant bias (p>0.05 in Mann-Whitney u-tests). This experiment demonstrated that these two lasers (i.e., short coherence length laser diode 12 and long coherence length laser 34) generated consistent results for the measurements of flow changes with both the DSCF detector (FIG. 8a) and the standard DCS detector (FIG. 8b). The consistency between the DSCF probe (i.e., short coherence length laser diode 12 used with bare CCD 14) and standard DCS probe (i.e., long coherence length laser 34 used with DCS detector fiber 32 and APD) measurements of flow changes (FIG. 8c) validated the new device and methodology (i.e., use of the DSCF probe).

Figure 9:
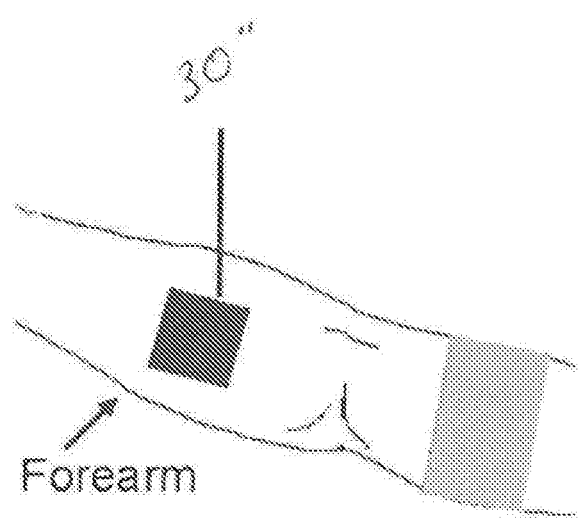
FIG. 9 is a forearm of a subject with a third dual contact probe testing the validity of the laser diode with the imaging device of the DSCF of FIG. 1.
Figure 10:
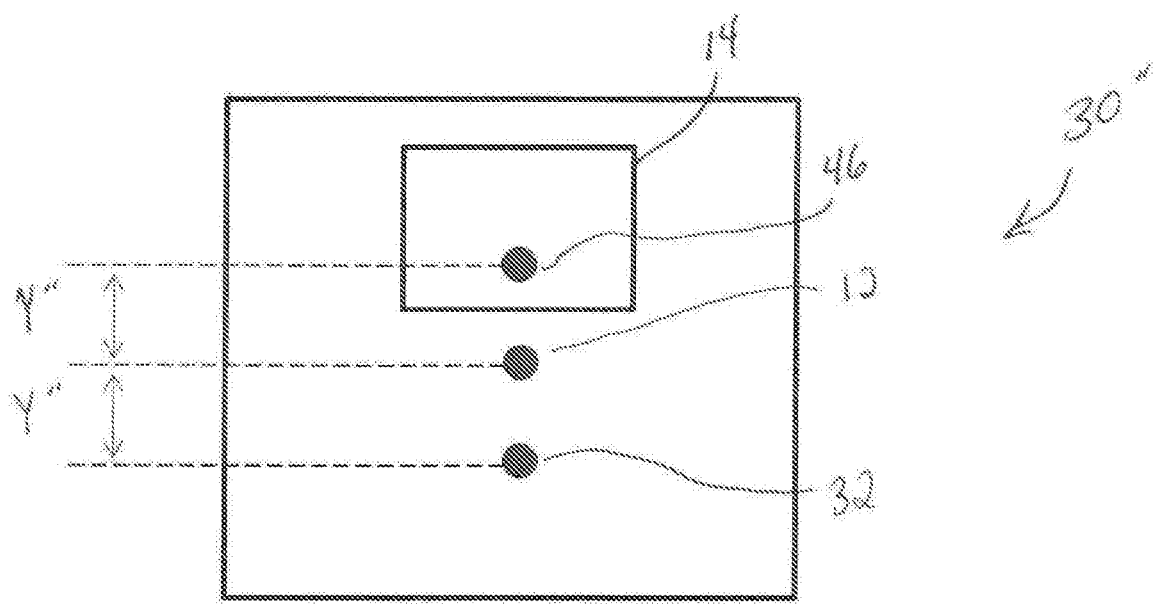
FIG. 10 is a schematic of the third dual contact probe of FIG. 9.
Figure 11A:
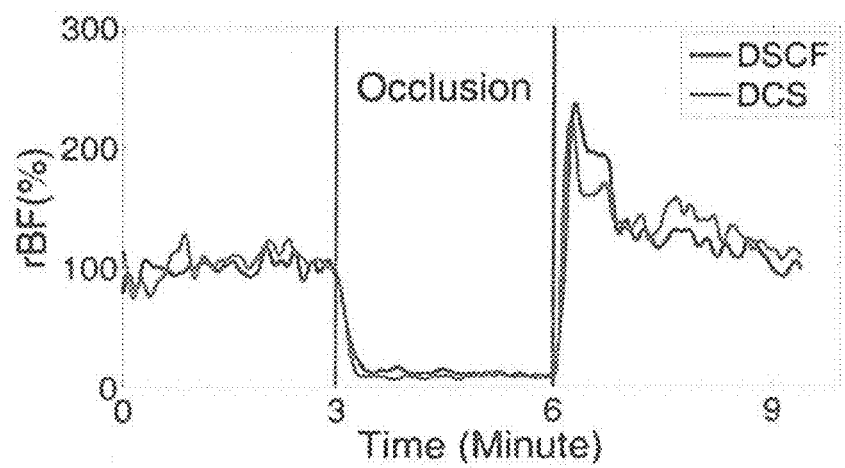
FIG. 11a is a plot of the time course of relative blood flow data measured concurrently by the imaging device of the DSCF and a DCS probe in the forearm before, during, and after the occlusion.

Further validation measurements in human tissues have also been conducted. A healthy subject was asked to sit and extend his right forearm on a table. With reference to FIG. 9, a dual contact probe 30", including the bare imaging device 14 (again using a CCD) of the DSCF probe as well as the DCS detector fiber 32 and APD of a standard DCS probe was utilized on the right forearm of the subject in order to measure concurrent BF measurements. The dual contact probe 30″ included a foam pad for receiving the bare imaging device 14, the DCS detector fiber 32, and the short coherence length laser diode 12, as shown in FIG. 10. As shown in FIG. 9, the dual contact probe 30″ and an arterial cuff were attached to the arm of the subject. An arterial cuff-occlusion (230 mmHg) paradigm was applied on subject's right upper arm to induce significant BF changes in the right forearm. The occlusion protocol included a 3-minute baseline, a 3-minute cuff inflation, and a 3-minute recovery period following the cuff deflation. The sampling rates for both DSCF and DCS measurements were set as 1 Hz (lower than the 2 Hz in tissue phantom experiments) in order to improve SNRs of BF measurements in human tissues. Data analyses were similar to those described in the tissue phantom experiments, and are illustrated in FIG. 11a and 1 lb. Relative blood flow (rBF) changes were normalized to the mean value of baseline BF data before the cuff-occlusion (assigning 100%).

Figure 11B:
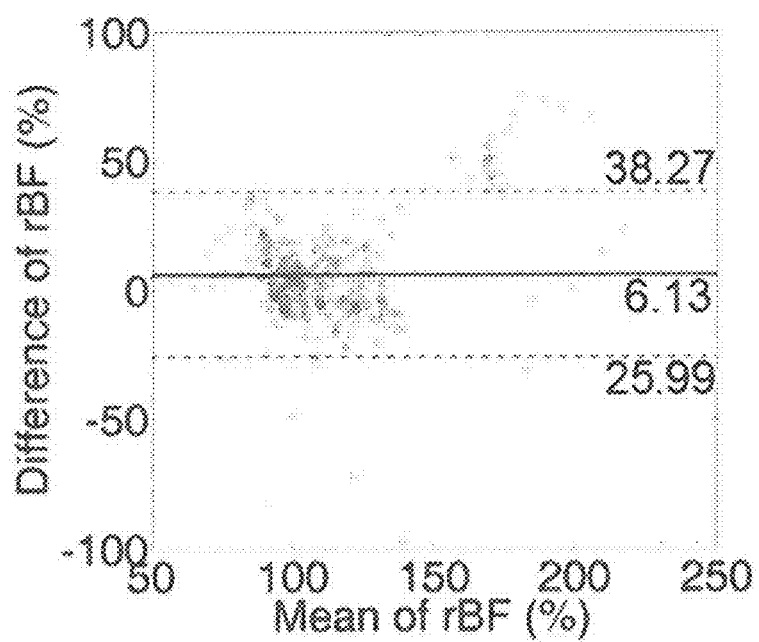
FIG. 11b is a Bland-Altman plot illustrating the results of the validity test of FIG. 9.

FIG. 11a shows the time course rBF data measured concurrently by the DSCF and DCS probes in the forearm before, during, and after the occlusion. The relatively lower limit of agreement observed in the forearm measurement (92.8% in FIG. 11b), as compared to those in the phantom tests, was likely due to heterogeneous reactive responses of blood flow in different regions/volumes of the forearm tissue measured by different probes. No significant bias was observed between the two measurements (p>0.05 in the Mann-Whitney u-test).

Figure 12:
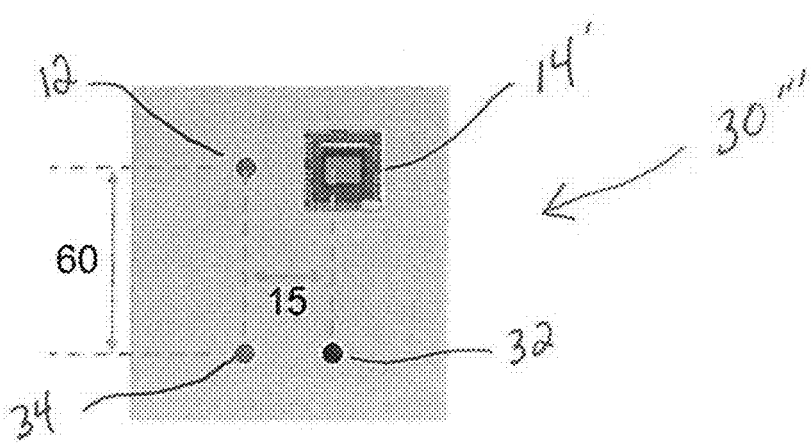
FIG. 12 is a schematic of a third dual contact probe for testing the validity of a low-power complementary metal oxide semiconductor (CMOS) based imaging device of a DSCF.
Figure 13A:
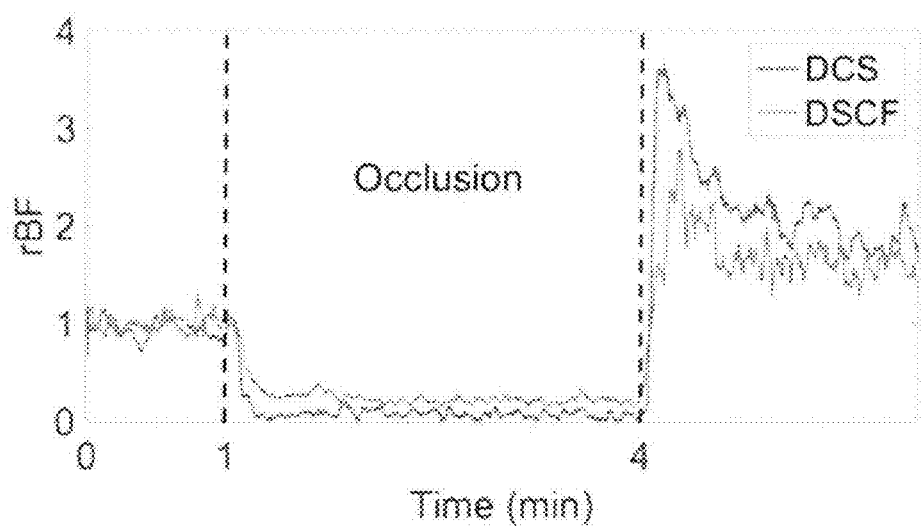
FIG. 13a is a plot of the time course of relative blood flow data measured concurrently by the CMOS based imaging device of FIG. 12 and a DCS probe in the forearm before, during, and after occlusion.
Figure 13B:
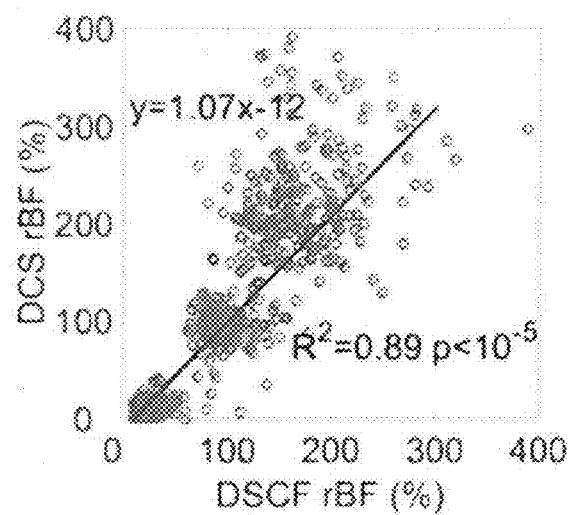
FIG. 13b is a plot of the relative blood flows of the DCS probe against the CMOS based imaging device of FIG. 12.

Similar validation protocols were followed with respect to the use of the imaging device 14 using the smaller, low-powered CMOS device as described above, for reduced heat generation. Illustrations of the validation experiment of the CMOS based imaging device 14 are illustrated in FIGS. 12 and 13a-13b. Therein, a healthy volunteer was asked to sit and extend his forearm on a table, as is illustrated in FIG. 9. A dual probe 30′″ included the CMOS imaging device 14′ and a standard DCS probe, both confined by a foam pad and taped on the forearm's surface for concurrent blood flow measurements. The S-D distance of 15 mm was used for both DSCF and DCS measurements (i.e. between both the laser diode 12 and CMOS imaging device 14′ as well as between the DCS laser 34 and the detector fiber 32 to the APD). The CMOS imaging device 14′ and the detector fiber 32 to the APD for use with DCS were place 60 mm apart. An arterial cuff-occlusion (230 mmHg) was applied on the upper arm to induce blood flow changes in the forearm. The relative blood flow (rBF) data before, during, and after the arterial occlusion are shown in FIG. 13a. As expected, a significant correlation ($R^2$=0.89, $p<10^{-5}$) and an excellent linear relationship (slope: 1.07%, intercept: 12.00%) between the DSCF and DCS measurements of rBF were observed (FIG. 13b). Bland-Altman analysis showed no significant bias with a good limit of agreement (93.9%), which is similar to our previous result (92.8%).

Figure 14:
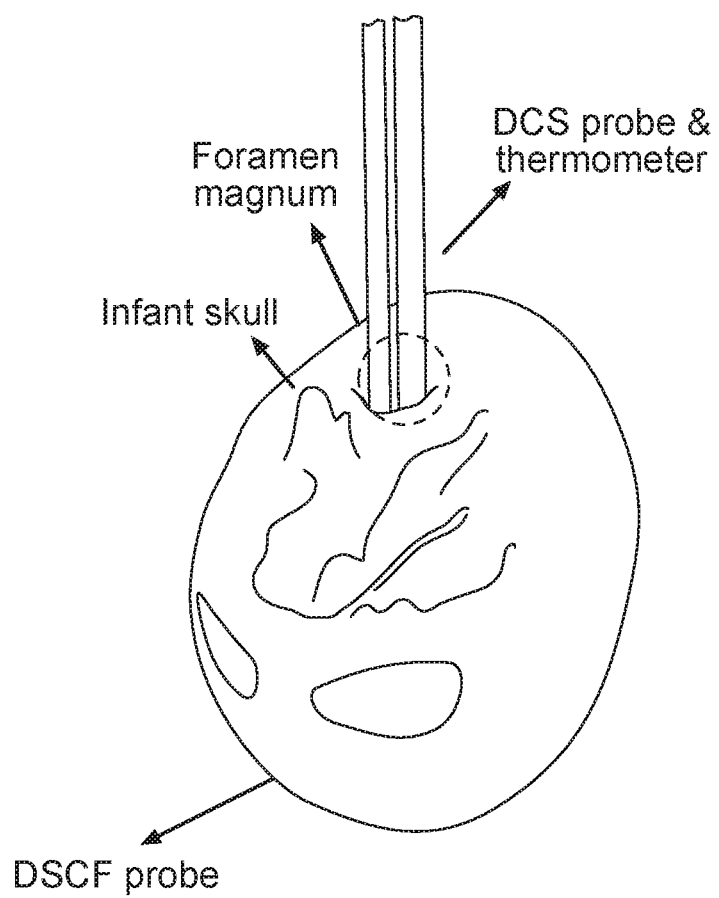
FIG. 14 illustrates the use of a DCS probe and a DSCF probe on an infant skull with a filled tissue-simulating liquid phantom.

In order to evaluate the ability of the DSCF probe 10 to make transcranial measurements through the superficial tissues of a head (e.g., infant skull), comparison measurements were conducted using the DSCF probe 10 and a standard DCS probe in a head-simulating phantom (FIG. 14). A realistic human infant skull (31 weeks of age) was kept inverted and filled with a turbid liquid solution mimicking the brain tissue. The homogenous liquid phantom comprised distilled water, India ink, and Intralipid, which has been extensively used for optical instrument calibrations. India ink is used to manipulate the absorption coefficient $\mu_a$ while Intralipid provides particle Brownian motion (flow) and control of the scattering coefficient $\mu_s'$. Flow variations of Intralipid particles were created by changing the phantom temperature, which was monitored by a thermocouple sensor (Physitemp) placed inside the phantom. The temperature was initially set up to ~50° C. by an immersed heater, and then decreased naturally until it reached ~30° C.

The data collected by the DSCF probe 10 (placed on the bottom of the inverted skull, FIG. 14) with two S-D distances (10 and 15 mm) at 8 different temperatures were analyzed using layer algorithms to correct partial volume artifacts from the skull (FIG. 15a) and compared to the conventional semi-infinite solutions with the S-D distances of 15 mm (FIG. 15b) and 10 mm (FIG. 15c), respectively. The layer algorithms are described in the following publications, the disclosures of which are incorporated herein by reference: 1) Shang Y, Li T, Chen L, Lin Y, Toborek M and Yu G, *Extraction of diffuse correlation spectroscopy flow index by integration of Nth-order linear model with Monte Carlo simulation*, Applied Physics Letters. 2014, 104: 193703; and 2) Shang Y and Yu G, *A Nth-order linear algorithm for extracting diffuse correlation spectroscopy blood flow indices in heterogeneous tissues*, Applied Physics Letters, 2014, 105:133702. The semi-infinite solutions are described in the following publications, the disclosures of which are incorporated herein by reference: 1) Shang Y, Cheng R, Dong L, Ryan S J, Saha S P and Yu G, *Cerebral monitoring during carotid endarterectomy using near-infrared diffuse optical spectroscopies and electroencephalogram*, Phys Med Biol., 2011; 56:3015-3032; 2) Cheng R, Shang Y, Hayes D, Saha S P and Yu G, *Noninvasive optical evaluation of spontaneous low frequency oscillations in cerebral hemodynamics*, Neuroimage, 2012; 62:1445-1454; and 3) Cheng R, Shang Y, Wang S Q, Evans J M, Rayapati A, Randall D C and Yu G, *Near-infrared diffuse optical monitoring of cerebral blood flow and oxygenation for the prediction of vasovagal syncope*, J Biomed Opt., 2014; 19.

Figure 15:
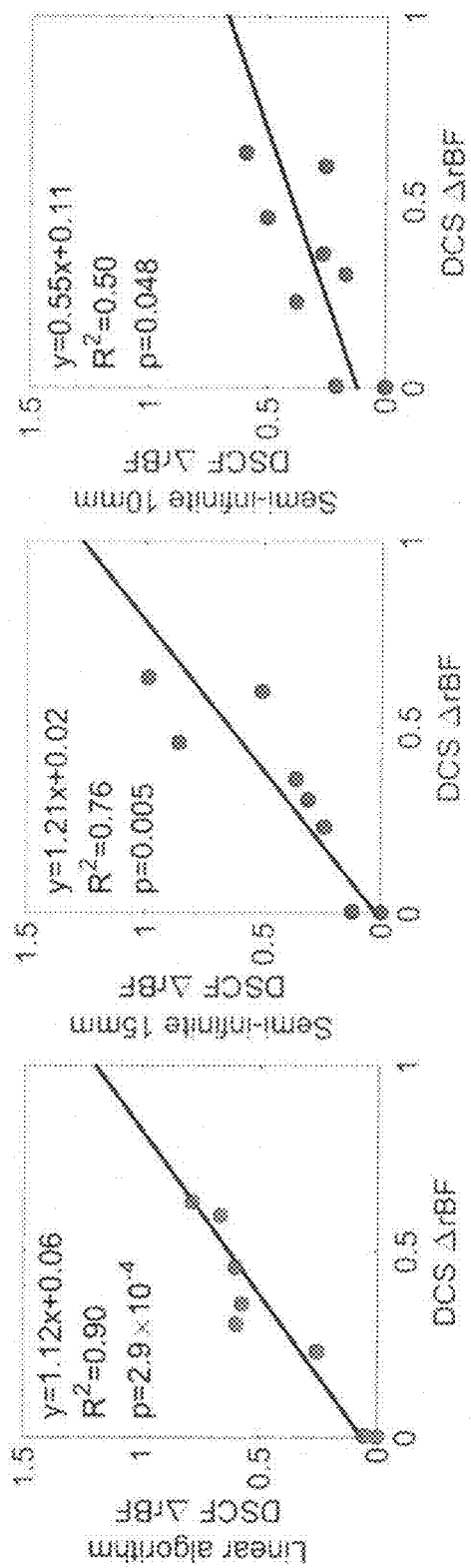
FIG. 15a is a plot of the relative flow changes as measured by the DSCF probe against those as measured by the DCS probe as calculated by a linear algorithm.
FIG. 15b is a plot of the relative flow changes as measured by the DSCF probe against those as measured by the DCS probe with a S-D distance of 15 mm as calculated by conventional semi-infinite solutions.
FIG. 15c is a plot of the relative flow changes as measured by the DSCF probe against those as measured by the DCS probe with a S-D distance of 10 mm as calculated by conventional semi-infinite solutions.

A fusiform shell matching the skull dimensions was used for Monte Carlo simulations required for the layer algorithms. The ΔrBF values were then compared to the "true" flow variations measured by the DCS probe (placed directly on the surface of Intralipid solution through the foramen magnum, FIG. 14) with a single S-D distance of 8 mm. A better correlation between DSCF and DCS measurements was observed with the layer algorithms (FIG. 15a) compared to the semi-infinite solutions without the correction of partial volume artifacts (FIG. 15b and FIG. 15c). As expected, partial volume artifacts from the skull had less influence on the measurements with larger S-D distance (FIG. 15b) than those with shorter distance (FIG. 15c). Bland-Altman analysis showed no significant bias with good limits of agreement for the layer algorithms (100%) and semi-infinite solutions at larger-distance (100%) and at shorter distance (87.5%).

These results demonstrate high consistency between DSCF and DCS measurements of flow changes in the human tissue and infant-head-simulating phantoms. Importantly, DSCF flow measurements with multiple S-D distances (such as may be provided by a high-resolution CMOS pixel array) can be performed transcranially through the superficial infant skull and the partial volume artifacts from the top skull layer can be significantly reduced using the linear layer algorithms noted above.

In contrast to noncontact CCD-based diffuse speckle contrast probes, the DSCF probe 10 allows for contact measurements of tissue BF variations, which can avoid potential motion artifacts and ambient light influence occurred in noncontact measurements. The major difference between the noncontact CCD detection scheme and contact DSCF is the way to use CCD: the noncontact CCD detection scheme uses a CCD camera with lenses without touching the tissue whereas the contact DSCF probe 10 uses a bare CCD chip 20 in contact with the tissue surface. The noncontact CCD probe with a zoom lens provides the flexibility to change the magnification and resolution of imaging, but should not affect the detection of BF. Therefore, the principles of noncontact CCD detection scheme and contact DSCF are essentially the same. The consistent results from our noncontact and contact CCD measurements of flow variations (FIG. 5a) support the commonality of these principles.

Compared to conventional contact DCS probes which commonly use rigid optical fibers for light delivery and detection, the compact DSCF probe 10 can be placed directly on the tissue surface without using any optical fiber. The connections between the DSCF probe and a control unit (including a driver for the laser diode and a laptop for CCD operation) are all electrical wires/cables, which provide the flexibility for probe installation and offer the potential for remotely longitudinal monitoring of tissue BF variations through wireless data transferring. Moreover, using an inexpensive laser diode 12 with a short coherence length and bare imaging chip 20 (such as a CCD or CMOS), the cost of a DSCF probe 10 significantly less than a conventional 4-channel DCS flowmeter that uses a long-coherence laser, a 4-channel APD module, and a 4-channel autocorrelator board (e.g. approximately $1,300 as compared to approximately $23,000). The cost-efficiency can be improved even more when conducting tomographic measurements as the single imaging chip of DSCF probe provides multiple detectors for image reconstruction.

In a further aspect of the invention, the DSCF technique can be extended to the use of multiple wavelengths to simultaneously measure multiple parameters, such as cerebral hemodynamic and metabolic parameters. These may include blood flow, blood oxygenation, oxygenation variations, $StO_2$, and $CMRO_2$, in deep tissues. This may be accomplished by using two or more laser diodes at different wavelengths. This results in a low-cost compact diffuse speckle contrast flow-oximeter (DSCFO). The principles of the DSCFO are similar to the DSCF, as indicated below.

Figure 16:
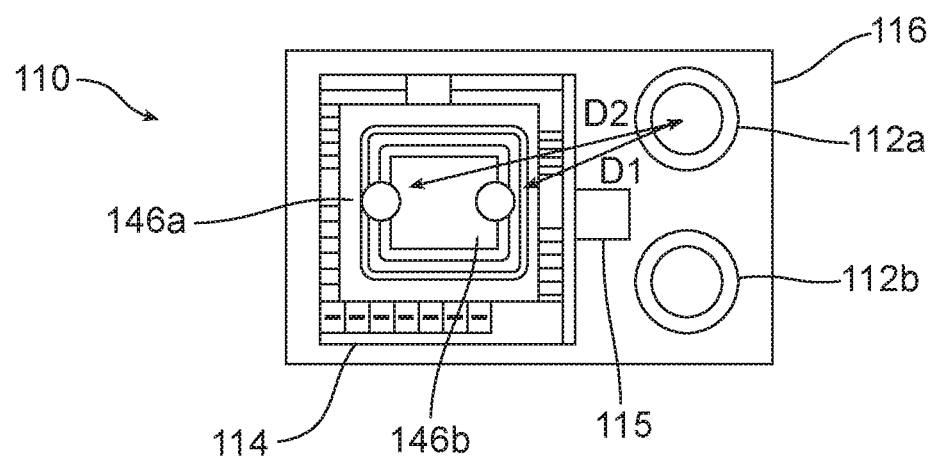
FIG. 16 is a schematic of a contact dual-wavelength diffuse speckle contrast flow-oximeter (DSCFO)

The DSCFO may comprise a DSCFO probe 110 including at least two laser diodes 112a and 112b, and a bare imaging device 114, as illustrated in FIG. 16. The laser diodes may output light at different wavelengths. The wavelengths may correspond to one or more particular parameters to be measured. For example, a first laser diode 112a may output a wavelength of 690 nm, at a power of 30 mW, and may have a diameter of 5.6 mm (e.g. HL6738MG, Thorlabs, NJ), while the second laser diode 112b may output a wavelength of 830 nm, at a power of 50 mW, and may have a diameter of 5.6 mm (e.g. HL8338MG, Thorlabs, NJ). The use of two laser diodes at such wavelengths may form a dual-wavelength flow-oximeter, which may maximize the sensitivity of $StO_2$ measurements. This is due to the different optical absorption characteristics of oxy-hemoglobin ($HbO_2$) vs. deoxy-hemoglobin (Hb). Other combinations of wavelengths may be used, such as 785 nm and 854 nm for measuring both blood flow and oxygenation.

The bare imaging device 114 may comprise a 2-dimensional array, such as a CCD or CMOS. In one aspect, the bare imaging device 114 comprises a CMOS chip (e.g. MU9PM-MBRD, Ximea), which may offer a 2592×1944 pixel array and may allow for an effective frame rate of 14 images per second. A 7×7 region of sensor pixels is the minimum requirement for conducting an effective BF measurement. Utilizing various subsets of pixels/detectors in the active-pixel array, the DSCFO probe 110 can take up to ~1,439,670 measurements per second. The high sampling rate allows several possible optimal modes to operate. For example, measurement accuracy can be increased by utilizing averaging data from multiple pixel/detector measurements, thereby reducing the impact of stochastic variation and sensor noise. Rapid multiple-channel measurements at different S-D distances enable the quantification of tissue hemodynamic heterogeneity at varying regions/depths of the head and reduction of partial volume artifacts from the scalp and skull. And pulsed operation can be employed in a manner that allows measurements to be taken intermittently (e.g., using a 1/14 duty cycle), thus significantly reducing power consumption and heat production. Other small-size, low-power, and/or high-sensitive CMOS sensors may be utilized in the DSCFO probe, such as NanEye (AWAIBA, Germany) or Spy Camera (Adafruit Industries, New York) to further reduce the probe size and heat production and to increase the detection sensitivity/depth.

The S-D distances may range between a first distance D1 and a second distance D2. These first and second distances D1, D2 may be characterized as the distances between a given laser diode 112a, 112b and a given detector 146a, 146b of the bare imaging device 114. As noted above, these detectors 146a, 146b may comprise a given 7×7 pixel region of the CMOS chip. In the illustrated embodiment of FIG. 16, the S-D distances may be 10 mm and 15 mm, respectively. S-D distances such as these allow measurements to be taken at sufficient depths (i.e. approximately half of the S-D distance, or 5-7.5 mm with the illustrated S-D distances) to penetrate the superficial layers of an infant's frontal scalp and skull. Moreover, multiple S-D distance measurements by the DSCFO probe allows for the reduction of partial volume artifacts from the top layer tissues using the linear layer algorithms noted above.

By alternatively measuring relative changes in intensities of given detectors at the two wavelengths, relative changes in tissue absorption coefficients $\Delta\mu_a(\lambda)$ can be extracted based on a dual-wavelength NIRS method, assuming that the tissue scattering coefficient $\mu_s'(\lambda)$ is known from the literature. This method is described in the following publication, the disclosure of which is incorporated herein by reference: Shang Y, Zhao, Y. Cheng, Y Dong L, Irwin D, Yu G, *Portable optical tissue flow oximeter based on diffuse correlation spectroscopy*, Optics Letters, 34(22), 3556-3558 (2009). Concentration changes of $\Delta[HbO_2]$ and $\Delta[Hb]$ can be determined from the measured $\Delta\mu_a(\lambda)$ at the two wavelengths and $\Delta StO_2$ (%) can be calculated from the ratio of $\Delta[HbO_2]/([HbO_2]+[Hb])$.

By alternatively measuring intensities of given detectors at the two wavelengths and at multiple different S-D distances, tissue absorption coefficients $\mu_a(\lambda)$ can be extracted based on a spatially-resolved (multiple S-D distances) NIRS method, assuming that the cerebral tissue scattering coefficient $\mu_s'(\lambda)$ is known from the literature. This method is described in the following publications, the disclosures of which are incorporated herein by reference: 1) Cheng R, Shang Y, Hayes D, Saha S P and Yu G, *Noninvasive optical evaluation of spontaneous low frequency oscillations in cerebral hemodynamics. Neuroimage,* 2012; 62:1445-1454; and 2) Liu H, Boas D A, Zhang Y, Yodh A G and Chance B, *Determination of optical properties and blood oxygenation in tissue using continuous NIR light*, Phys Med Biol., 1995; 40:1983-93. Concentrations of $[HbO_2]$ and $[Hb]$ can be determined from the measured $\mu_a(\lambda)$ at the two wavelengths and $StO_2$ (%) can be calculated from the ratio of $[HbO_2]/([HbO_2]+[Hb])$.

Averaged blood flow index (BFI) at the two wavelengths represents a CBF value. The relative change in $CMRO_2$ can be calculated based on Fick's law, $rCMRO_2=rCBF\times(1-StO_2)/(1-StO_{2base})$, where $StO_{2base}$ is the baseline $StO_2$ before physiological changes. This method is described in the following publications, the disclosures of which are incorporated herein by reference: 1) Shang Y, Zhao Y, Cheng R, Dong L, Irwin D and Yu G. *Portable optical tissue flow oximeter based on diffuse correlation spectroscopy*, Opt Lett., 2009; 34:3556-3558; 2) Shang Y, Cheng R, Dong L, Ryan S J, Saha S P and Yu G. *Cerebral monitoring during carotid endarterectomy using near-infrared diffuse optical spectroscopies and electroencephalogram*, Phys Med Biol., 2011; 56:3015-3032; 3) Cheng R, Shang Y, Hayes D, Saha S P and Yu G. *Noninvasive optical evaluation of spontaneous low frequency oscillations in cerebral hemodynamics*, Neuroimage, 2012; 62:1445-1454; 4) Gurley K, Shang Y and Yu G. *Noninvasive optical quantification of absolute blood flow, blood oxygenation, and oxygen consumption rate in exercising skeletal muscle*, J Biomed Opt., 2012; 17:075010; 5) Shang Y, Li T, Chen L, Lin Y, Toborek M and Yu G. *Extraction of diffuse correlation spectroscopy flow index by integration of Nth-order linear model with Monte Carlo simulation*, Applied Physics Letters, 2014; 104: 193703; 6) Shang Y and Yu G. *A Nth-order linear algorithm for extracting diffuse correlation spectroscopy blood flow indices in heterogeneous tissues*, Applied Physics Letters, 2014; 105 133702; 7) Cheng R, Shang Y, Wang S Q, Evans J M, Rayapati A, Randall D C and Yu G. *Near-infrared diffuse optical monitoring of cerebral blood flow and oxygenation for the prediction of vasovagal syncope*, J Biomed Opt. 2014; 19; 8) Shang Y, Chen L, Toborek M and Yu G. Diffuse optical monitoring of repeated cerebral ischemia in mice. Opt Express. 2011; 19:20301-20315; 9) Chen L, Shang Y, Sipos K E, Saatman K E, Yu G and Toborek M. *Novel experimental model for repeated forebrain ischemia-reperfusion*, Journal of experimental stroke and translational medicine, 2012; 5:1-10.

As further illustrated in FIG. 16, the DSCFO probe may include a thermocouple 115. This may be used for evaluating the temperature of the surface of the tissue being evaluated.

A retainer 116 may be provided for maintaining relative position between the laser diodes 112a, 112b and the bare imaging device 114. The retainer 116 may be in the form of a pad, a plate, a block, or a film, which may include one or more receivers for receiving the laser diodes 112a, 112b and the bare imaging device 114. For example, the retainer 116 may comprise a foam pad with an aperture or retaining space for each of the laser diodes 112a, 112b and the bare imaging device 114.

A 3D printer may be used to fabricate the probe. Each sensor element (e.g. the CMOS chip and the thermocouple) and the laser diodes may be assembled with rubber-like photopolymers (e.g. PolyJet photopolymers) to form a soft surface that is suitable for long-term use. In one aspect, the soft surface may be adapted to conform to the surface curvature of a neuronal forehead.

Figure 17:
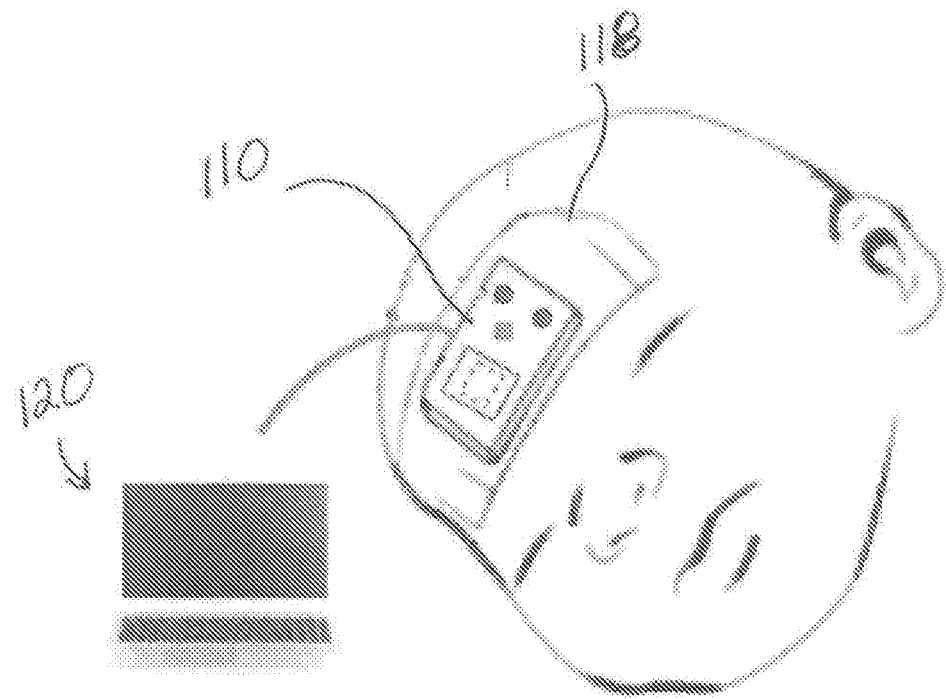
FIG. 17 illustrates the use of the dual-wavelength DSCFO of FIG. 16 on an infant cranium.

As can be seen in FIG. 17, in use, the DSCFO probe 110 may be attached to a fixing element 118, such as medical tape, a bandage, or other adhesive strip, for retaining the probe in contact with the surface of the tissue. The DSCFO probe 110 may be connected to a controller, such as a computer, a laptop, or other mobile device, and power-supply circuitry elements.

While the invention has been described with reference to specific examples, it will be understood that numerous variations, modifications and additional embodiments are possible, and all such variations, modifications, and embodiments are to be regarded as being within the spirit and scope of the invention. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. A probe for use in measuring a hemodynamic parameter deep within a tissue of a subject, said probe comprising:
   a light source comprising a laser diode for emitting near-infrared light into the tissue of the subject to provide point illumination; and
   a detector comprising a two-dimensional pixel array adapted to contact the tissue of the subject and receive diffuse light fluctuations reflected from the tissue to detect diffuse laser speckle contrast variations in the tissue for measurement of the hemodynamic parameter; wherein the light source and the detector are separated by a known source-detector ("S-D") distance that is approximately twice the desired penetration depth of the light source in a tissue, the detector being connected to a controller adapted to calculate a blood flow index from measured diffuse laser speckle contrast at the S-D distance by a diffusive model with a multiple scattering theory, and further wherein said probe includes no optical cable.

2. The probe of claim 1, further including a retainer for retaining the light source laser diode and the detector at the known S-D distance fixed positions relative to each other.

3. The probe of claim 2, wherein the retainer is selected from the group consisting of a block, a plate, a film or a foam pad.

4. The probe of claim 1, wherein the laser diode produces a coherence length in human tissue larger than 10 cm and 1 m.

5. The probe of claim 1, wherein the detector is adapted to receive the light reflected from the tissue without passing through any lenses prior to receiving the light.

6. The probe of claim 1, wherein the known S-D distance is a distance of between 0 mm-20 mm.

7. The probe of claim 1, wherein the controller is remote from the source and detector.

8. The probe of claim 1, wherein the controller is connected to the source and detector via electrical wires.

9. The probe of claim 1, wherein the controller is connected to the source and detector via electrical wires.

10. The probe of claim 1, wherein the two-dimensional pixel array comprises a bare charge coupled device.

11. The probe of claim 1, wherein the two-dimensional pixel array comprises a complementary metal oxide semiconductor.

12. The probe of claim 1, further comprising an optical lens.

13. The probe of claim 1, wherein the S-D distance is such that the probe can measure blood flow approximately up to 10 mm below tissue surface.

14. A method of measuring at least one hemodynamic parameter within a tissue of a subject, said method comprising:

placing the probe of claim 1 on surface tissue above the skull of the subject, wherein the two-dimensional pixel array of the detector is in contact with the tissue of the subject;

emitting near-infrared light from the laser diode onto tissue of the subject, said near-infrared light not received through an optical cable; and measuring diffuse light from the tissue and calculating through the controller a blood flow index from measured diffuse laser speckle contrast at the S-D distance by a diffusive model with a multiple scattering theory.

15. The method of claim 14, further including the step of emitting light at a second wavelength from a second laser diode within the light source into the tissue, and wherein the measuring step comprises measuring reflected diffuse laser speckle contrast reflected from the tissue from the first laser diode and the second laser diode, alternatively.

16. The method of claim 14, further including the step of attaching each of the light sources and the detector to a retainer in order to maintain the S-D distance.

17. The method of claim 16, wherein the S-D fixed distance is between 0 mm and 20 mm.

18. A probe for use in measuring at least one hemodynamic parameter within a tissue of a subject, said probe comprising:

a light source comprising a first laser diode adapted for emitting near-infrared light into the tissue of the subject at a first wavelength to provide a first point of illumination and a second laser diode adapted for emitting a second point of illumination into the tissue of the subject at a second wavelength different from the first laser diode;

a detector comprising a two-dimensional pixel array adapted to contact the tissue of the subject and receive diffuse light reflected from the tissue to detect diffuse laser speckle contrast variations in the tissue for measurement of the hemodynamic parameter; and a retainer adapted to receive and maintain a known source-detector ("S-D") distance from each of the first laser diode and the second laser diode to the detector, said retainer including a contact surface adapted to contact the tissue of the subject;

wherein the retainer is adapted to maintain the source and detector in contact with the tissue with no lens therebetween.

19. The probe of claim 18, wherein the probe includes no optical cable.

20. The probe of claim 18, wherein the two-dimensional pixel array comprises a charge coupled device.

21. The probe of claim 18, wherein the two-dimensional pixel array comprises a bare complementary metal oxide semiconductor.

22. The probe of claim 18, wherein the S-D distance is such that the probe can measure blood flow approximately up to 10 mm below tissue surface.

* * * * *

UNITED STATES PATENT AND TRADEMARK OFFICE
CERTIFICATE OF CORRECTION

PATENT NO. : 10,842,422 B2  
APPLICATION NO. : 15/655988  
DATED : November 24, 2020  
INVENTOR(S) : Guoqiang Yu, Chong Huang and Jeffrey Todd Hastings Page 1 of 1

It is certified that error appears in the above-identified patent and that said Letters Patent is hereby corrected as shown below:

In the Claims

Claim 2, Line 36: delete "laser diode"

Claim 2, Line 37: delete "fixed positions relative to each other"

Claim 4, Lines 42-43: delete "and 1 m"

Claim 10, Line 56: delete "bare"

Claim 15, Line 16: delete "reflected"

Claim 17, Line 22: delete "fixed"

Claim 21, Line 23: delete "bare"

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*